US 6,670,174 B1

(12) United States Patent
Smith et al.

(10) Patent No.: US 6,670,174 B1
(45) Date of Patent: Dec. 30, 2003

(54) CULTURE DISH PACKAGE AND METHOD OF MAKING

(75) Inventors: Jerry W. Smith, Ann Arbor, MI (US); Nadine M. Sullivan, Ann Arbor, MI (US); Ruth F. Eden, Ann Arbor, MI (US)

(73) Assignee: Difco Laboratories Incorporated, Ann Arbor, MI (US)

( * ) Notice: Subject to any disclaimer, the term of this patent is extended or adjusted under 35 U.S.C. 154(b) by 0 days.

(21) Appl. No.: 07/873,634

(22) Filed: Apr. 23, 1992

Related U.S. Application Data

(63) Continuation of application No. 07/492,888, filed on Mar. 12, 1990, now abandoned.

(51) Int. Cl.[7] .................................................. C12M 1/22
(52) U.S. Cl. .............................. 435/305.4; 435/303.2; 435/305.1
(58) Field of Search .............................. 436/1; 206/815, 206/569, 499, 551; 220/669, 671, 674, 675; 435/297, 298, 809, 810, 299, 300, 305.4, 303.2, 305.1

(56) References Cited

U.S. PATENT DOCUMENTS

| | | | | |
|---|---|---|---|---|
| 796,558 A | * | 8/1905 | Bowman | 206/815 |
| 2,874,091 A | * | 2/1959 | Fisk | 435/810 |
| 2,971,850 A | * | 2/1961 | Barton | 435/810 |
| 2,971,892 A | * | 2/1961 | Carski | 435/298 |
| 3,351,264 A | * | 11/1967 | Bostrom | 206/499 |
| 3,562,114 A | * | 2/1971 | Steidl et al. | 435/809 |
| 3,576,721 A | * | 4/1971 | Mason | 435/809 |
| 3,751,341 A | * | 8/1973 | Seitz et al. | 435/810 |
| 4,038,148 A | * | 7/1977 | Miller et al. | 435/810 |
| 4,072,577 A | * | 2/1978 | Hirshaut | 435/810 |
| 4,262,091 A | * | 4/1981 | Cox | 435/297 |
| 4,384,972 A | * | 5/1983 | Nakamura et al. | 422/40 |
| 4,419,451 A | * | 12/1983 | Garner et al. | 435/298 |
| 4,605,617 A | * | 8/1986 | Kasugai | 422/61 |
| 4,709,819 A | * | 12/1987 | Lattuada et al. | 435/297 |
| 4,728,608 A | * | 3/1988 | Roberts et al. | 435/810 |

* cited by examiner

*Primary Examiner*—Jan Ludlow
(74) *Attorney, Agent, or Firm*—Kohn & Associates, PLLC

(57) ABSTRACT

A culture package system comprising a package preferably in the form of a container containing one or more conventional culture media dishes containing solidified culture media. Each dish includes a bottom wall and a peripheral side wall and a removable cover having a bottom wall and a peripheral side side wall which is loosely telescoped over the dish. A plurality of the dishes are preferably provided in inverted stacked relation in the container. A cover is hermetically sealed to close the container. The interior of the package has a gaseous atmosphere having less than 1% oxygen. An oxygen absorber is placed in the package to facilitate maintaining the atmosphere at less than 1% oxygen. Preferably a moisture absorber is also placed in the package. The package is made of plastic material which is impermeable to oxygen and moisture and preferably is in the form of a container which has a base wall and a peripheral wall and a cover sealed thereto.

11 Claims, 4 Drawing Sheets

CULTURE DISH PACKAGE AND METHOD OF MAKING

"This is a continuation of application(s) Ser. No. 07/492,888 filed on Mar. 12, 1990, now abandoned and which designated the U.S."

FIELD OF THE INVENTION

This invention relates to sterile culture media dishes.

BACKGROUND AND SUMMARY OF THE INVENTION

It is old and well known to utilize culture media in a container for conducting growth and biochemical reactions, wherein the sample of the specimen to be tested is applied to the surface of the medium in the container. Such devices are commonly known as Petri dishes or plates.

Commonly used Petri dishes in the form of a dish having a bottom wall and a peripheral side wall are filled with the molten culture medium and rapidly cooled to solidify or gel. A cover is loosely applied. In order to prevent surface phenomenon problems such as contamination and condensation of moisture, it has been essential to refrigerate such Petri dishes until they are to be used. Contamination occurs because the cover is loosely applied allowing entrance and exchange of external non-sterile atmospheres.

Syneresis which is the separation of liquid from a gel occurs because of evaporation and contraction of the culture medium and the inability of the expelled liquid to rehydrate the solidified gel. When there is a temperature differential between the inside of the dish and the environment, the effect of this evaporation on the inside cover results in heavy condensation and necessitates that a technician must first dry the interior of the plate before using it. Dehydration occurs more rapidly with warmer temperatures and dry conditions in the environment.

U.S. Pat. No. 4,262,091 shows a method for providing Petri dishes of a culture medium in an oxygen-free manner. The empty culture dishes require prior anaerobic storage, and the dishes are stored, filled and packaged under anaerobic conditions. This process is extremely cumbersome and expensive especially for high volume production of culture dishes.

In an effort to reduce or prevent problems with sterility and dehydration, it has been common to provide a, plurality of such Petri dishes in a sterile plastic sealed bag. However, it has still been essential to refrigerate the package for most types of culture media to retard syneresis, contamination and dehydration. Refrigeration has also been necessary for culture media which are subject to oxidation such as those that contain blood, vitamins or antibiotics. Further, refrigeration may be required for extended storage greater than a week. Currently, the shelf life of such culture dishes is very limited, and is on the order of three or four months. Accordingly, it has been necessary to date the package. As a result, if the package is not used within the time indicated it must be destroyed. In addition, the manner in which the dishes are packaged does not protect them from breakage.

Therefore, there is a need for a system which is more convenient and does not require that dishes be placed in anaerobic storage before being filled with medium; in which the dishes may be filled with a medium in a conventional manner under ambient conditions; which provides a package system that is designed to protect the dishes from breakage; which allows ease of transportation of the dishes; and which permits visual inspection prior to use.

Among the objectives of the present invention are to provide a culture media package which has a long shelf life; which minimizes the problems of syneresis, desiccation, and contamination; which does not require refrigeration; which can be readily shipped; which is not fragile; which can be utilized in a conventional manner as in the well known art of using Petri dishes; which is low in cost; which can be produced relatively rapidly; which is transparent, allowing for visual inspection prior to use; and which is pleasing in appearance and which will withstand shipping and handling without special precautions.

In accordance with the invention, a culture package system comprises a package such as a container containing one or more conventional culture media dishes containing solidified culture media. Each dish includes a bottom wall and a peripheral side wall and a removable cover having a bottom wall and a peripheral side side wall which is loosely telescoped over the dish. A plurality of the dishes are preferably provided in inverted stacked relation in a package, such as a container. A cover is hermetically sealed to close the container. An oxygen absorber is placed in the package to facilitate maintaining the atmosphere at a low oxygen level. The interior of the package has a gaseous atmosphere having minimal oxygen content, preferably less than 1% oxygen. Preferably a moisture absorber is also sealed in the package. In addition, a color indicator is preferably sealed within the package to indicate by change of color when the oxygen level within the container exceeds a predetermined value.

The container is made of plastic material which is impermeable to oxygen and moisture and is preferably in the form of a container which has a base wall and a peripheral wall. The container preferably includes means for preventing movement of the dishes laterally. The peripheral wall preferably has a series of ribs which are concave inward and a series of ribs which are concave outward and disposed around the circumference of the peripheral wall. The inwardly concave ribs are constructed and arranged to contact the exterior surface of the dishes and to engage and cushion the dishes so as to prevent breakage. The outwardly concave ribs facilitate placement of the absorbers into the container and removal of the dishes from the container. Preferably a partial vacuum exists within the container causing the cover to flex into engagement with the stack of dishes and hold the dishes firmly within the container.

In accordance with the invention there is also provided a method of making the sterile package system including a package preferably in the form of a container containing a plurality of culture media dishes, each dish including a bottom wall and a peripheral side wall and a removable cover having a bottom wall and a peripheral side wall telescoped over the dish. The method comprises the steps of:

1) filling the dishes successively with a culture medium,
2) successively drying the head space above the media, by sterile, low humidity air, without the need to cool the dishes,
3) applying a cover successively to each dish,
4) thermoforming successive containers of plastic material comprising a base wall and a peripheral wall,
5) inserting a plurality of covered dishes in stacked inverted relation in each container,
6) inserting an oxygen absorber packet and optionally a moisture absorber packet into the container, 7) preferably flushing the containers with an oxygen free gas, and 8) sealing a plastic top on each container.

Preferably, the package system is made by thermoforming successive containers from a strip of thermoplastic material to provide a strip of interconnected containers. The cover is also preferably made from a continuous strip of plastic material. The containers are successively filled with a plurality of the conventional culture media dishes and the oxygen absorber packet, the optional moisture absorber packet and the color indicator packet are inserted. The oxygen and moisture absorber packets are preferably placed in the container after the culture medium dishes are placed into the package. A stream of oxygen free gas is then used to flush the package, and the containers are successively sealed by the cover. The packages are then successively severed from the strip.

In the method of making a package system to provide stability and increased shelf life, the culture dishes may be filled with medium in an aerobic atmosphere, that is, without the necessity for providing an anaerobic atmosphere. In addition, the package can be made without the necessity of cooling by refrigeration. Preferably, the containers are flushed with a nitrogen gas, thereby creating anaerobic conditions in the container. Advantageously, the use of nitrogen gas is very cost effective and therefore no catalysts or gases containing hydrogen are required in the manufacturing process. The oxygen absorber, preferably in the form of a packet, maintains a low oxygen environment within the container.

The atmosphere in the package system is preferably less than ambient atmospheric pressure to secure the plates within the package. When the pressure is less than ambient, the flexible top is flexed inwardly such that it lies tightly against the stack of plates, preventing them from moving about within the package. This helps protect the plates from breakage.

DETAILED DESCRIPTION OF THE DRAWINGS

DETAILED DESCRIPTION OF THE EMBODIMENT

Figure 1:
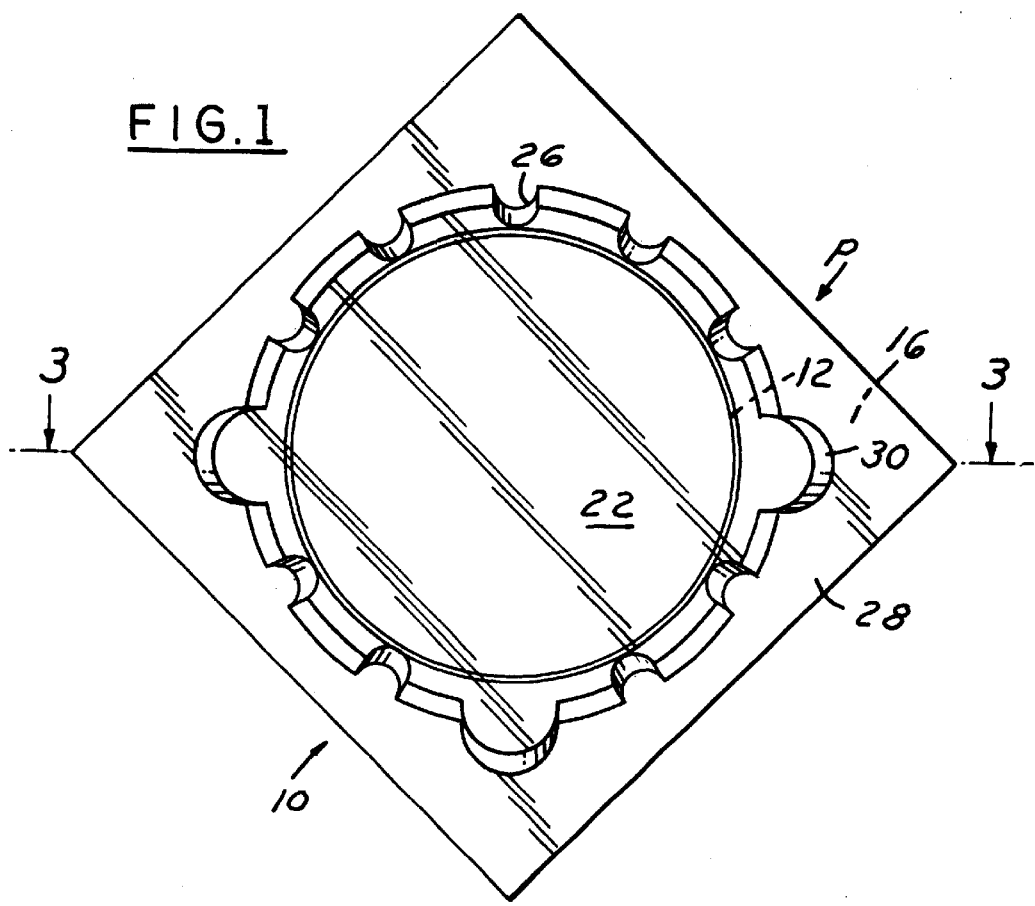
FIG. 1 is a plan view of a sterile package system containing a plurality of culture media dishes and stabilizing agents.

Referring to FIGS. 1–5, the sterile package system P embodying the invention comprises a package, preferably a plastic container 10 containing one or more conventional culture media dishes 12, each of which contains solidified culture media and a cover 14 loosely provided on the dish. The package system P further includes a cover 16 hermetically sealed within the container 10. The interior of the container 10 has a gaseous atmosphere preferably less than 1% oxygen. An oxygen absorber packet 18 is placed in the container 10 to facilitate maintaining the oxygen at less than 1%. Optionally, a moisture absorber packet 20 is provided in the container. The oxygen absorber packet may include the color indicator or optionally the color indicator may be provided in a separate packet.

The container 10 comprises a base wall 22 and a peripheral wall 24. The peripheral wall 24 has a plurality of circumferentially spaced, axially extending hollow ribs 26 disposed around the circumference of said peripheral wall 24. The ribs 26 are inwardly concave and are constructed and arranged to contact the exterior surface of the dishes 12 and to engage and cushion the dishes 12.

Figure 2:
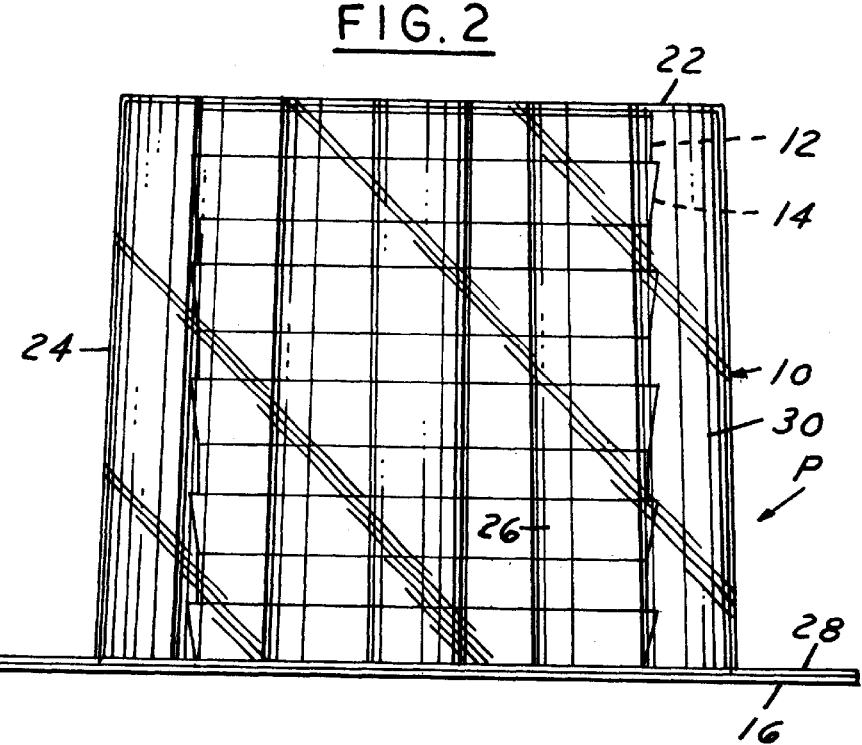
FIG. 2 is a side view of the sterile package system.
Figure 3:
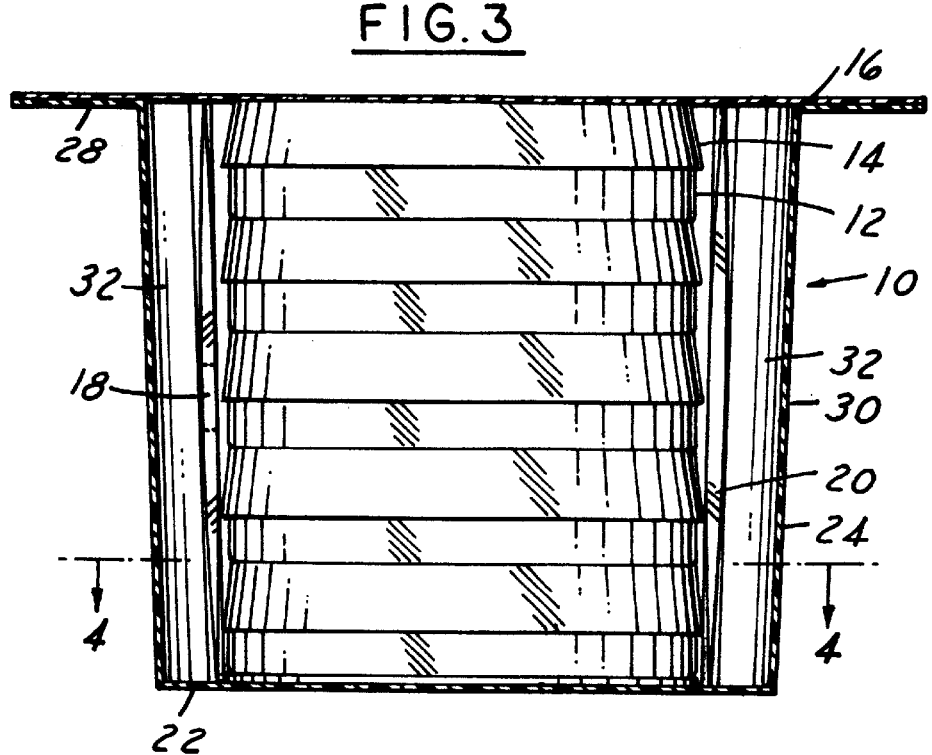
FIG. 3 is a sectional view taken along line 3—3 of FIG. 1.
Figure 5:
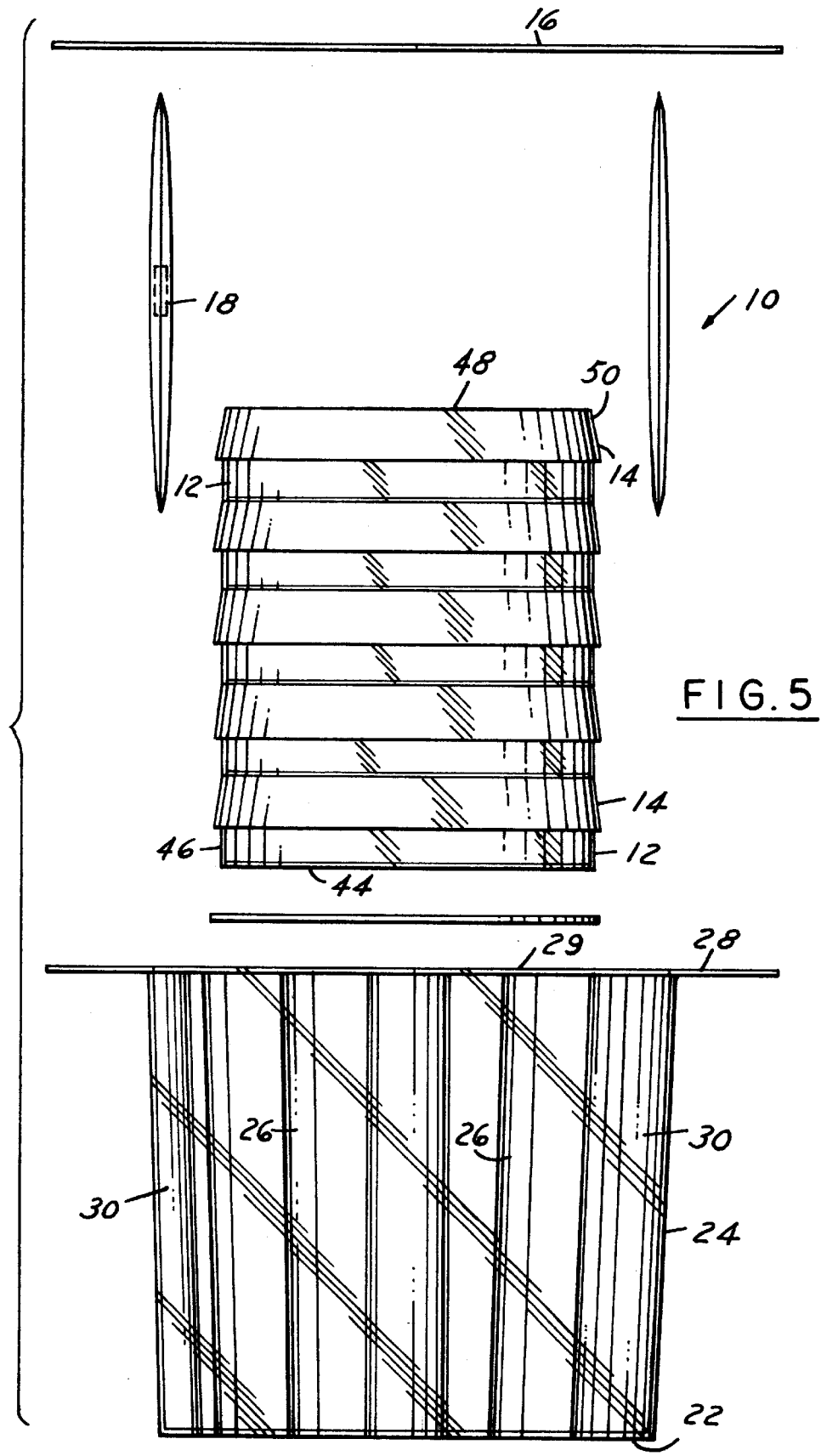
FIG. 5 is an exploded view of the sterile package system.

As shown in FIGS. 2, 3 and 5, preferably, the peripheral wall 24 tapers axially and outwardly from said base wall 22, for example, the angle of taper is 2° to 3°. The container 10 also includes a peripheral flange 28 that extends radially outwardly from the open end 29 of the peripheral wall 24.

Figure 4:
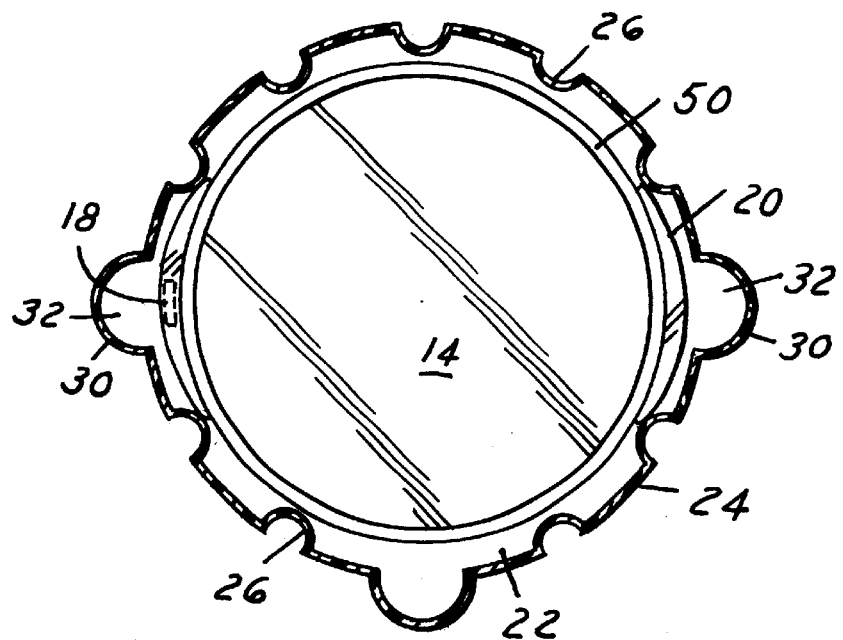
FIG. 4 is a sectional view taken along line 4—4 of FIG. 3.

As shown in FIGS. 1 and 4, the peripheral wall 24 also includes at least one axially extending hollow rib 30 which is outwardly concave. The outwardly concave ribs 30 are larger than the inwardly concave ribs 26 so as to facilitate the placement of dishes into the container 10 and the removing of dishes from the container 10 and to facilitate the placement of media stabilizing agents such as packets 18, 20 in the channels 32 provided by said outwardly concave ribs 30, adjacent the exterior surface of the dishes.

The interior diameter defined by ribs 26 is about equal to the maximum diameter of the dishes 12. The container 10 preferably has a height sufficient to contain a plurality of dishes 12 and preferably, three to five dishes are accommodated in the container 10.

The container 10 is constructed of a plastic material which is composed of a material which is relatively impervious to oxygen and moisture and will retain a substantially oxygen free atmosphere. The material can be a monolithic structure such as PET or PETG or amorphous nylon, or it can be a multilayered structure with one layer for stiffness (PET, PETG), one layer for barrier (EVOH) and one layer for sealability (Surlyn, EVA, polyethylene). Other materials may comprise the nitrites sold under the trademark BAREX™.

The total shelf life of the package system will depend upon the degree of impermeability of the plastic material to oxygen and moisture and the amount of oxygen absorber in the package which is preferably the sealed container. Although, as indicated below, the containers may be flushed with an oxygen free gas before sealing, sufficient oxygen absorber may be provided within the sealed container such as to provide the necessary oxygen free atmosphere shortly after the container is sealed. Thus, the relative impermeability of the plastic material and the amount of oxygen absorber are combined to maintain the level of oxygen within the container below a predetermined value for a predetermined period of time resulting in a predetermined shelf life of the package system.

Preferably, the thermoformable material 40 is provided in a continuous sheet or strip such that the container 10 may be formed in a continuous process.

Preferably, the cover 16 of the package system P is made from a continuous plastic foil or sheet material which is composed of materials having the same characteristics as the container 10. The material may consist of PET or other suitable formable material, which is relatively rigid and transparent.

The media stabilizing agents, such as oxygen absorbers and moisture absorbers, are used to increase shelf life. The agents include an oxygen absorber 18 and a moisture absorber 20. The oxygen absorber 18 is used to control the oxidative process that causes degradation of the biological medium. The preferred oxygen absorber is in a sachet form which is convenient and easy for loading into the concave outward portions 30 of the container 10. Oxygen absorbers, sometimes referred to as deoxidizers, include powdery iron, ascorbic acid and a calcium hydroxide activator and activated carbon. Examples include a deoxidizer sold by Mitsubishi of Japan under the trademark Ageless™, and the deoxidizers described in U.S. Pat. No. 4,605,617. The moisture absorber 20 is a material which does not "pull" water actively from the medium but rather absorbs moisture after it has been formed in the package. The moisture absorber 20 controls and maintains a constant relative humidity. Examples of moisture absorbers include cellulose based materials such as soft wood and cotton fibers and combinations thereof, such as the desiccant paper sold by Multiform Desiccants, Inc. under the trademark Natrasorb®. Other examples are calcium containing compounds, and molecular sieve materials such as zeolites, which are also available from Multiform Desiccants, Inc. Examples of color indicators are well-known indicators containing powered materials that change in color such as methylene blue, phenazine, a Co complex of a Schiff base composed of salicylaldehyde and diamines, all of which change color when a predetermined amount of oxygen is present. Conveniently, the moisture absorbers, oxygen absorbers and color indicators are available in gas and moisture permeable packets of various sizes which are formed from plastic or paper.

Desirably, a packet 20 is inserted into the container 10 after it is formed and before the dishes 12 are placed therein. Preferably, the package system P also comprises an inert gas 42 which is injected into the container 10, after the dishes 12 and packet 20 are placed into the container 10 and just prior to applying and sealing the cover 16. Preferably the atmosphere in the package is less than ambient atmospheric pressure. When the pressure is less than ambient, the cover is flexed inwardly such that it lies tightly against the stack of plates, preventing them from moving about within the package.

In accordance with the invention there is also provided a method of making the sterile package system including a package which is preferably a container 10 containing a plurality of culture media dishes 12, each dish 12 including a bottom wall 44 and a peripheral side wall 46 and a removable cover 14 having a bottom wall 48 and a peripheral side wall 50 telescoped over the dish 12. The method comprises the steps of:

1) filling the dishes 12 successively with a culture medium,
2) successively drying the head space above the media, by sterile, low humidity air, without the need to cool the dishes 12,
3) applying a cover 14 successively to each dish 12,
4) thermoforming successive containers of plastic material comprising a base wall 22 and a peripheral wall 24,
5) inserting a plurality of covered dishes 12 in stacked inverted relation in each container 10,
6) inserting an oxygen absorber packet 18 and optionally a moisture absorber 20 packet and optionally a color indicator into the container 10,
7) preferably flushing the containers 10 with an oxygen free gas, and
8) sealing a plastic cover 16 on each container 10.

Figure 6:
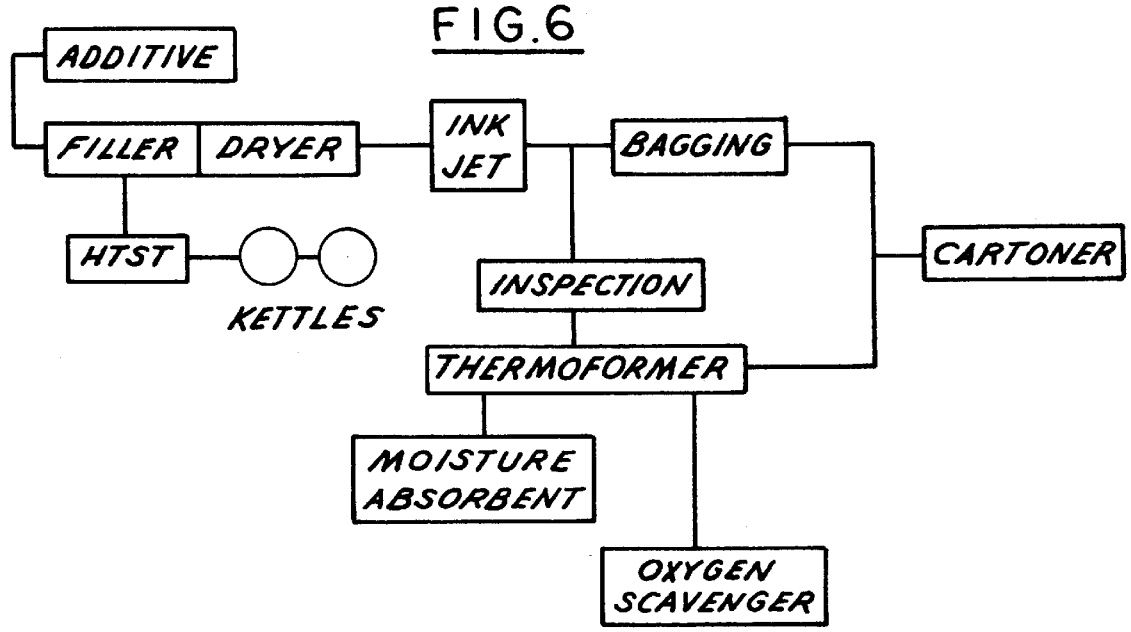
FIG. 6 is a schematic view of the method of making a sterile package system containing a plurality of culture media dishes.

Referring to FIG. 6, the method does not require an anaerobic atmosphere.

Figure 7:
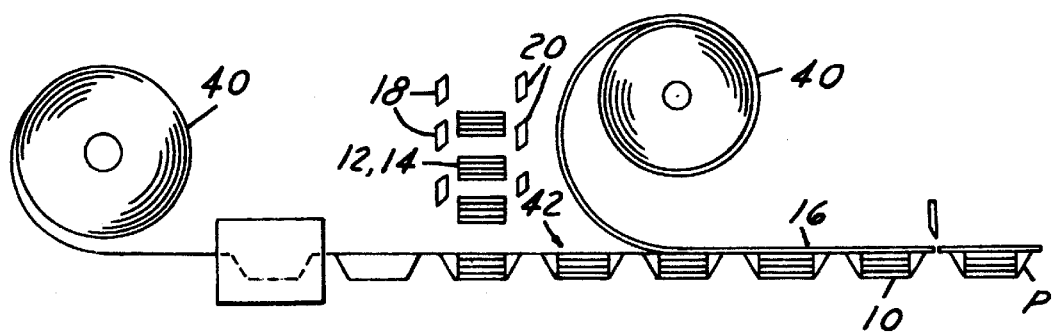
FIG. 7 is a schematic view of a portion of the schematic providing added detail for the view shown in FIG. 6.

In the method, the dishes 12 are filled, solidified, and dried such that condensation and moisture from the filling process are minimized. Conventional culture dishes 12 are filled, for example, with molten agar which then is permitted to solidify and then a stream of sterile low-humidity air is passed over the dish to "dry" the excess moisture evaporating from the surface of the dish. After the dish surface is dried, the cover 14 is again applied to the dish 12 which is then conveyed to the next station for labelling. From the labelling station the dishes are manually inspected, stacked in a specified number and conveyed to the thermoforming station. Referring to FIG. 7, at the thermoforming station the container 10 is formed. The culture dishes 12 are placed into the formed plastic container 10. An active oxygen absorber 18 and optionally a moisture absorber 20 and optionally a color indicator are placed into the container 10 either before or after the culture medium dishes 12 are placed into the container 10. The container 10 is sealed by a cover 16 in the form of a continuous roll, which is brought over the open end 29 of the container 10. A stream of oxygen-free gas 42, preferably nitrogen, is then flushed into the container 10 immediately prior to hermetically sealing the container 10 and cover 16. The packages are die cut, labelled, and packed in suitable cartons for shipping.

EXAMPLE I

Bismuth sulfite agar is used for the isolation of Salmonella from environmental sources. This culture medium is extremely sensitive to oxidative degradations. The proposed processing of this culture medium for stabilization includes: filling a conventional petri dish, drying the moisture from the surface, placing the medium into a container after a moisture absorber and oxygen absorber has been placed into the container. The container is flushed with oxygen-free nitrogen before the container is hermetically sealed with a heat sealer.

The initial oxygen concentration is less than 1% within 6 hours to 12 hours.

With maintenance of the environment of less than 1% oxygen, the performance of the plate continues beyond 60 days stored at 37° C. (or 120 days at 25° C.). In a similar container but packaged and stored with ambient amounts of oxygen, biological performance becomes poor within 4 days at 37° C. storage.

EXAMPLE II

Blood agar culture media has a short shelf life of 8 to 12 weeks refrigerated. The proposed processing of this culture medium is the same as in Example I, namely: filling a conventional petri dish, drying the moisture from the surface, placing the medium into a container after a moisture absorber and oxygen absorber has been placed into the container. The container is flushed with oxygen-free nitrogen before the container is hermetically sealed with a heat sealer.

The color of the blood within the container changes from bright red to dark "burgundy" red indicating reduced oxygen conditions. The low oxygen atmosphere extends the life of the red cells within the culture medium such that growth and test reactions are evident after seven months of storage at room temperature.

It can thus be seen that there has been provided a culture media package has a long shelf life; minimizes the problems of syneresis, desiccation, and contamination; does not require refrigeration; can be readily shipped; is not fragile; can be utilized in a conventional manner as in the well known art of using petri dishes; is low in cost; can be produced relatively rapidly; is transparent, allowing for visual inspection prior to use; and is pleasing in appearance.

We claim:

1. A culture media system comprising: at least one culture media container, containing a material consisting essentially of non-prereduced culture media, said culture media being subject to degradation by exposure to oxygen, moisture loss and syneresis; a package made of material at least substantially impermeable to oxygen and moisture enclosing said container; means for sealing said package; and an active oxygen absorber sealed within said package for actively scavenging oxygen that permeates through said package and residual oxygen contained in said media, to prevent degradation of said media such that said media has an extended shelf life.

2. The culture media package system set forth in claim 1 wherein said package is made of transparent plastic material.

3. The culture media package system set forth in claim 1 wherein said gaseous atmosphere in said package surrounding said containers has an oxygen content of less than 1%.

4. The culture media package system set forth in claim 1 wherein the amount of oxygen absorber is sufficient to maintain the oxygen content within said package at a predetermined level for a predetermined period of time.

5. The culture media system set forth in claim 1 wherein said oxygen absorber means comprises a permeable packet containing the oxygen absorber.

6. The culture media system set forth in claim 5 wherein the amount of said oxygen absorber means being such that said atmosphere in said package has an oxygen content of less than 1%.

7. The culture media system set forth in claim 1 wherein said package contains atmosphere sealed therein, said system further including a moisture absorber sealed in said package, the amount of moisture absorber being of the type and sufficient to absorb moisture from said atmosphere sealed in said package after it is formed in the atmosphere to maintain a constant relative humidity in the atmosphere of said package during said predetermined period.

8. The culture media system set forth in claim 7 wherein said moisture absorber comprises a solid material.

9. The culture media system set forth in claim 1 wherein said container is made of transparent plastic material.

10. The culture media system set forth in claim 1 wherein said container includes means engaging a stack of culture media dishes to inhibit lateral movement thereof.

11. The culture media system set forth in claim 1 wherein said package contains a gaseous atmosphere, said gaseous atmosphere after sealing of the package has an oxygen content of less than 1% and the amount of oxygen absorber is sufficient to reduce the oxygen content to the desired level with a predetermined time after filing.

* * * * *